(12) United States Patent
Nakamura et al.

(10) Patent No.: US 10,677,731 B2
(45) Date of Patent: Jun. 9, 2020

(54) METHOD OF MANUFACTURING SENSING CHIP AND SENSING CHIP

(71) Applicant: KONICA MINOLTA, INC., Chiyoda-ku, Tokyo (JP)

(72) Inventors: Yukito Nakamura, Tokorozawa (JP); Takatoshi Kaya, Inagi (JP); Tomonori Kaneko, Hachioji (JP); Kosuke Nagae, Kodaira (JP); Hiroshi Hirayama, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 146 days.

(21) Appl. No.: 15/558,506

(22) PCT Filed: Apr. 5, 2016

(86) PCT No.: PCT/JP2016/061112
§ 371 (c)(1),
(2) Date: Sep. 14, 2017

(87) PCT Pub. No.: WO2016/170967
PCT Pub. Date: Oct. 27, 2016

(65) Prior Publication Data
US 2018/0080872 A1    Mar. 22, 2018

(30) Foreign Application Priority Data

Apr. 22, 2015    (JP) ................. 2015-087588

(51) Int. Cl.
*G01N 21/64* (2006.01)
*G01N 21/03* (2006.01)
(Continued)

(52) U.S. Cl.
CPC ........... *G01N 21/648* (2013.01); *G01N 21/03* (2013.01); *G01N 21/64* (2013.01);
(Continued)

(58) Field of Classification Search
CPC .. G01N 21/648; G01N 21/6428; G01N 21/03; G01N 21/64; G01N 21/552;
(Continued)

(56) References Cited

U.S. PATENT DOCUMENTS 5,923,031 A * 7/1999 Naya .................... G01N 21/553
                                                  250/227.25
6,274,872 B1    8/2001 Katerkamp
(Continued)

FOREIGN PATENT DOCUMENTS

EP    1324019 A1    7/2003
JP    10239233 A    9/1998
(Continued)

OTHER PUBLICATIONS

International Search Report (ISR) and Written Opinion dated Jun. 21, 2016 issued in International Application No. PCT/JP2016/061112.
(Continued)

*Primary Examiner* — Michael L Hobbs
(74) *Attorney, Agent, or Firm* — Holtz, Holtz & Volek PC

(57) ABSTRACT

A first frame having a first through-hole is arranged on a support so that one opening of the first through-hole is closed. A liquid containing a capturer is fed into the first through-hole, and a capturer is immobilized on the support exposed in the first through-hole. After removing the liquid from the support, a second frame having the second through-hole is arranged on the support in the first through-hole so that one opening of the second through-hole is closed.

11 Claims, 7 Drawing Sheets

(51) Int. Cl.
*G01N 33/543* (2006.01)
*G01N 21/552* (2014.01)

(52) U.S. Cl.
CPC ....... *G01N 21/6428* (2013.01); *G01N 33/543* (2013.01); *G01N 33/54373* (2013.01); *G01N 21/552* (2013.01); *G01N 2021/6439* (2013.01); *G01N 2021/6482* (2013.01); *G01N 2201/0612* (2013.01)

(58) Field of Classification Search
CPC .......... G01N 33/54373; G01N 33/543; G01N 2201/0612; G01N 2021/6482; G01N 2021/6439; B01L 7/52; B01L 3/502707; B91L 2300/1827; B91L 2300/1861; B91L 2300/0893; C12Q 1/686
See application file for complete search history.

(56) References Cited

U.S. PATENT DOCUMENTS

| | | | |
|---|---|---|---|
| 7,027,159 | B2 | 4/2006 | Naya |
| 9,551,662 | B2 | 1/2017 | Kaya |
| 2003/0156292 | A1 | 8/2003 | Naya |
| 2004/0091397 | A1* | 5/2004 | Picard ................ B01D 67/0088 422/400 |
| 2006/0194345 | A1 | 8/2006 | Uchiyama et al. |
| 2010/0075300 | A1* | 3/2010 | Miller .............. G01N 33/54373 435/5 |
| 2010/0252751 | A1 | 10/2010 | Klunder et al. |

FOREIGN PATENT DOCUMENTS

| | | |
|---|---|---|
| JP | 2000515966 A | 11/2000 |
| JP | 2011503536 A | 1/2011 |
| JP | 2013076673 A | 4/2013 |
| JP | 2014119418 A | 6/2014 |
| WO | 2005022155 A1 | 3/2005 |
| WO | 2012157403 A1 | 11/2012 |

OTHER PUBLICATIONS

European Office Action dated Dec. 14, 2018 issued in European Application No. 16782988.6.
Schramm, et al., "Strategies for the Immobilization of Antibodies", Immunmethods, Oct. 1, 1993, vol. 3, No. 2, pp. 93-103.
Extended European Search Report (EESR) dated Mar. 20, 2018 issued in counterpart European Application No. 16782988.6.
Japanese Office Action (and English language translation thereof) dated Jan. 7, 2020 issued in Japanese Application No. 2017-154051.

* cited by examiner

METHOD OF MANUFACTURING SENSING CHIP AND SENSING CHIP

TECHNICAL FIELD

The present invention relates to a method of manufacturing a sensing chip for detecting a substance to be detected and a sensing chip.

BACKGROUND ART

When a trace amount of a substance to be detected such as protein and DNA can be quantitatively detected with high sensitivity in clinical examinations or the like, it is possible to rapidly check the condition of the patient and to treat a disease. For this reason, there is a demand for a detection apparatus capable of detecting a trace amount of a substance to be detected quantitatively with high sensitivity.

As a detection apparatus capable of detecting a substance to be detected with high sensitivity, there is known a device utilizing surface plasmon resonance fluorescence spectroscopy (Surface Plasmon-field enhanced Fluorescence Spectroscopy: hereinafter, abbreviated as "SPFS") (for example, refer to Patent Literature 1).

In the detection apparatus disclosed in Patent Literature 1, used is a sensing chip (sensor structure) having a sensor member and a well member immobilized on the sensor member. The sensor member includes a prism (dielectric member), a metal film formed on the prism, and a reaction field (ligand immobilization region) which is a region where a capturer (ligand) formed on the metal film for capturing a substance to be detected (analyte) is immobilized. The well member has a through-hole at a position corresponding to the reaction field. By arranging the well member on the sensor member, a well for storing a sample solution is formed. In the detection apparatus, the capturer captures the substance to be detected in the reaction field in the well, and the captured substance to be detected is labeled with a fluorescent substance. In this state, when the metal film is irradiated with excitation light through the prism at an angle at which surface plasmon resonance occurs, localized field light can be generated on the surface of the metal film. By the localized field light, the fluorescent substance that labels the substance to be detected captured on the metal film is selectively excited, and fluorescence light is emitted from the fluorescent substance. By detecting the fluorescence light, the detection apparatus can detect the presence or amount of the substance to be detected.

In the sensing chip, if the substance to be detected adheres to an inner wall surface of the through-hole of the well member, the detection efficiency is lowered. In order to prevent the problem, the sensing chip disclosed in Patent Literature 1 is manufactured by immobilizing the capturer on the entire surface of the metal film, and after that, arranging the well member on the metal film or by immobilizing the capturer on a portion of the surface of the metal film by using a frame member having a through-hole, and after that, removing the frame member and newly arranging the well member on the metal film. By manufacturing the sensing chip in this manner, it is possible to prevent the capturer from being immobilized on the inner wall surface of the through-hole of the well member.

CITATION LIST

Patent Literature

Patent Literature 1: WO 2012/157403 A

SUMMARY OF INVENTION

Technical Problem

However, in the method of manufacturing the sensing chip disclosed in Patent Literature 1, when the capturer is immobilized on the entire surface of the metal film, an excessive amount of the capturer is used, which causes an increase in production cost. In addition, in a case where the capturer is immobilized on a portion of the surface of the metal film by using the frame member, since a step of removing the frame member not constituting the sensing chip is required, the manufacturing process becomes complicated.

An object of the present invention is to provide a method of manufacturing a sensing chip capable of preventing immobilization of a capturer on an inner wall surface of a well without using a frame member that does not constitute a sensing chip and the sensing chip manufactured by the method.

Solution to Problem

To solve the above problem, a method of manufacturing a sensing chip according to an embodiment of the present invention is a method of manufacturing a sensing chip used for detecting a substance to be detected in a specimen, including: a step of arranging a first frame having a first through-hole on a support so that one opening of the first through-hole is closed; a step of feeding a liquid containing a capturer for capturing a substance to be detected in the first through-hole and immobilizing the capturer on the support exposed in the first through-hole; and a step of removing the liquid from the support, and after that, arranging a second frame having a second through-hole on the support in the first through-hole so that one opening of the second through-hole is closed.

To solve the above problem, a sensing chip according to an embodiment of the present invention is a sensing chip used for detecting a substance to be detected in a specimen, including: a support; a first frame having a first through-hole and arranged on the support so that one opening of the first through-hole is closed; and a second frame having a second through-hole and arranged on the support in the first through-hole so that one opening of the second through-hole is closed, wherein a capturer for capturing the substance to be detected in the specimen is immobilized on at least a portion of an inner wall surface of the first through-hole of the first frame and on a surface of the support exposed in the first through-hole.

Advantageous Effects of Invention

According to a method of manufacturing a sensing chip according to the present invention, it is possible to easily manufacture a sensing chip in which a capturer is not immobilized on an inner wall surface of a well without using a frame member that does not constitute the sensing chip. By using the sensing chip obtained by the present invention, it is possible to detect a substance to be detected with high sensitivity and high accuracy while suppressing a loss of the substance to be detected due to adhesion to the inner wall surface of the well.

DESCRIPTION OF EMBODIMENTS

Hereinafter, embodiments of the present invention will be described in detail with reference to the drawings. In the following description, a surface plasmon enhanced fluorescence detection apparatus (hereinafter, also referred to as an "SITS apparatus") for detecting a substance to be detected by using surface plasmon resonance (SPR) will be described as a representative example of a detection apparatus.

Figure 1:
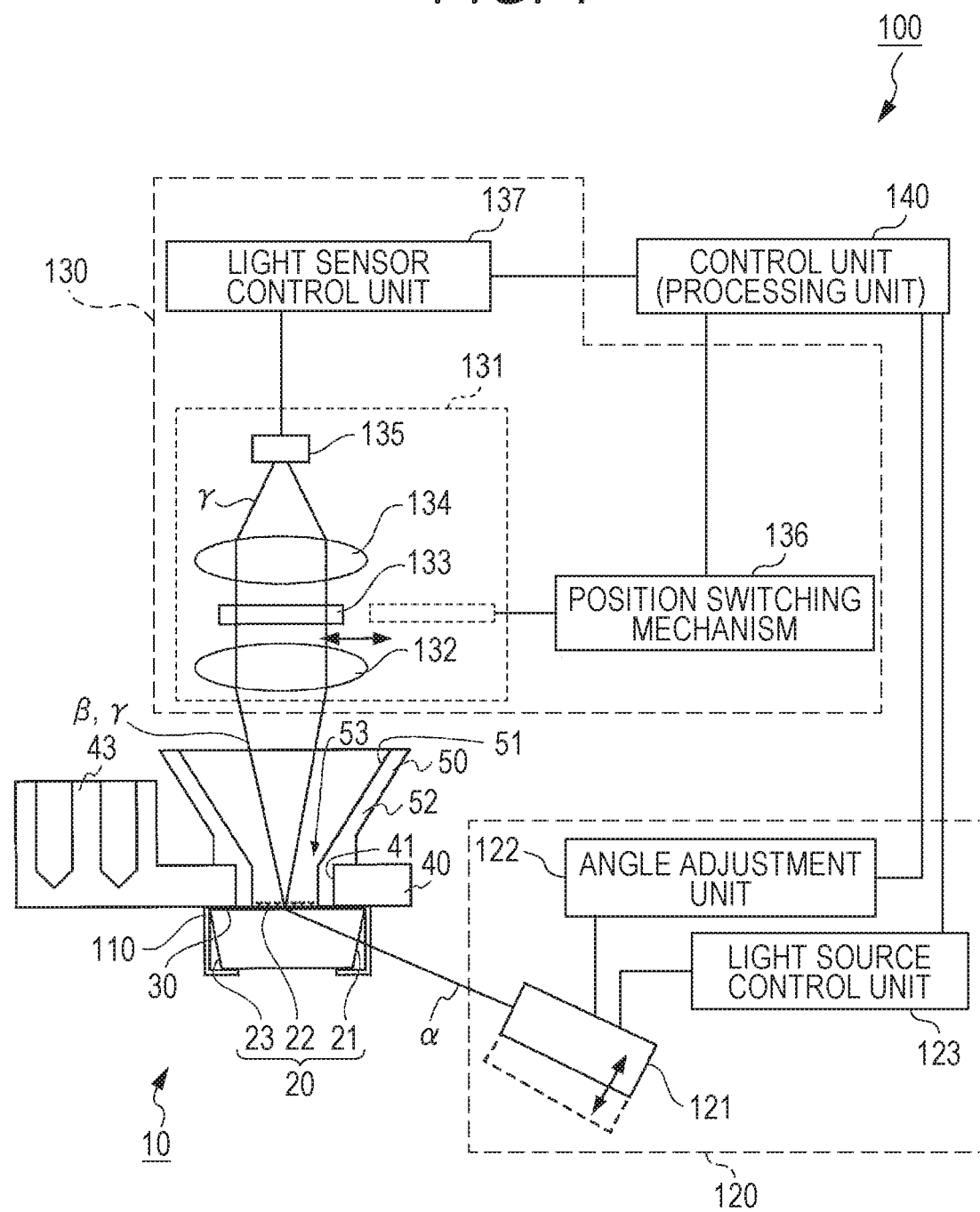
FIG. 1 is a diagram illustrating a configuration of a surface plasmon enhanced fluorescence detection apparatus.

FIG. 1 is a diagram illustrating a configuration of an SPFS apparatus 100. In FIG. 1, hatching is omitted in order to illustrate paths of light. As illustrated in FIG. 1, the SPFS apparatus 100 is configured to include a chip holder 110 for detachably holding a sensing chip 10, a light irradiation unit 120 for irradiating the sensing chip 10 with light, a light receiving unit 130 for detecting light (plasmon scattered light β or fluorescence light γ) emitted from the sensing chip 10, and a control unit (processing unit) 140 for controlling these components. The SPFS apparatus 100 is used in the state where the sensing chip 10 is mounted on the chip holder 110. The sensing chip 10 will be described first, and each component of the SPFS apparatus 100 will be described thereafter.

(Configuration of Sensing Chip)

Figure 2A:
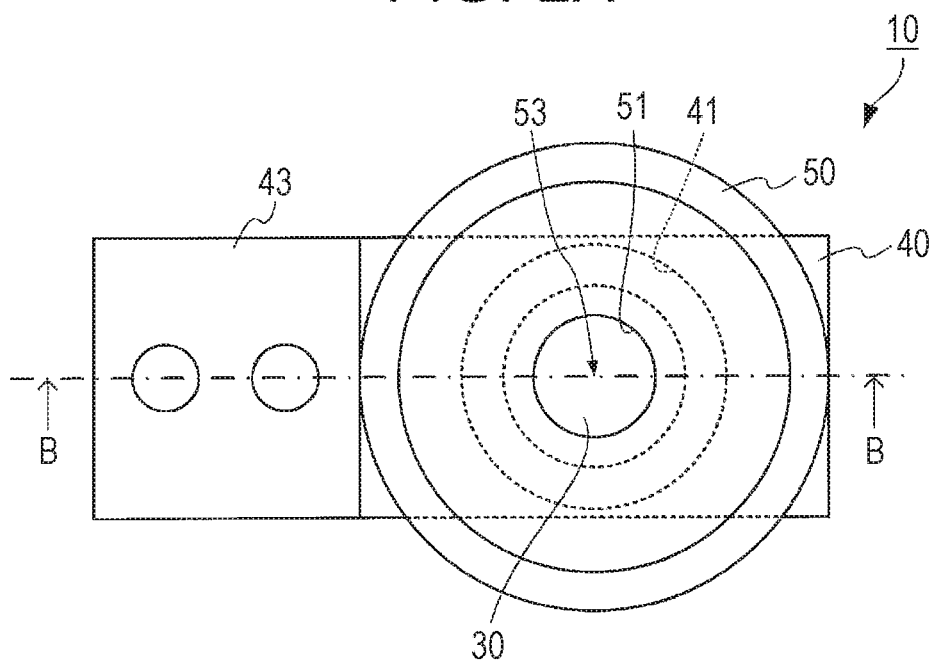
FIGS. 2A and 2B are diagrams illustrating a configuration of a sensing chip according to an embodiment of the present invention.
Figure 2B:
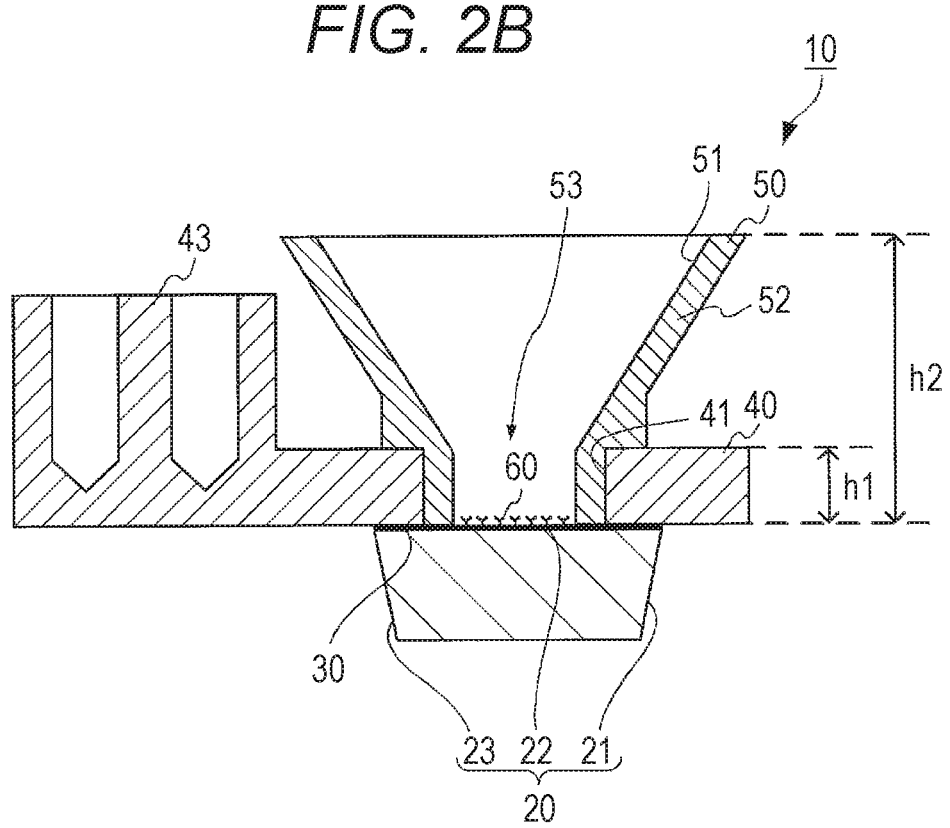

FIGS. 2A and 2B are diagrams illustrating a configuration of the sensing chip 10 according to the embodiment, FIG. 2A is a plan diagram of the sensing chip 10, and FIG. 2B is a cross-sectional diagram taken along line B-B in FIG. 2A. As illustrated in FIGS. 2A and 2B, the sensing chip 10 is configured to include a prism (support) 20 having an incidence surface 21, a film formation surface 22, and a light emission surface 23 and having a metal film 30 formed on the film formation surface 22, a first frame 40 arranged on the metal film 30 and having a first through-hole 41, and a second frame 50 arranged in the first through-hole 41 on the metal film 30 and having a second through-hole 51. By arranging the second frame 50 on the prism 20 so that one opening of the second through-hole 51 is closed, a well 53 for accommodating a liquid is formed.

The prism 20 is made of a dielectric material that is transparent to excitation light α. As described above, the prism 20 has the incidence surface 21, the film formation surface 22, and the light emission surface 23.

The incidence surface 21 allows the excitation light α from the light irradiation unit 120 to be incident into the interior of the prism 20. The metal film 30 is arranged on the film formation surface 22. The excitation light α incident into the interior of the prism 20 is reflected by the metal film 30. More specifically, the excitation light α is reflected at the interface (the film formation surface 22) between the prism 20 and the metal film 30. The light emission surface 23 emits the excitation light α reflected by the metal film 30 to the outside of the prism 20.

The shape of the prism 20 is not particularly limited. In the embodiment, the shape of the prism 20 is a columnar body having a trapezoid as a bottom surface. The surface corresponding to one bottom side of the trapezoid is the film formation surface 22, the surface corresponding to one leg is the incidence surface 21, and the surface corresponding to the other leg is the light emission surface 23. The trapezoid which is the bottom surface is preferably an isosceles trapezoid. Therefore, the incidence surface 21 and the light emission surface 23 are symmetrical, and the S-wave component of the excitation light α is hard to stay in the prism 20. The incidence surface 21 is formed so that the excitation light α does not return to the light irradiation unit 120. This is because, in a case where the light source of the excitation light α is a laser diode (hereinafter, also referred to as an "LD"), when the excitation light α returns to the LD, the excited state of the LD is disturbed, and thus, the wavelength and output of the excitation light α fluctuate. Therefore, in the scanning range centered on an ideal resonance angle or enhancement angle, the angle of the incidence surface 21 is set so that the excitation light α is not incident perpendicularly on the incidence surface 21.

Herein, the "resonance angle" denotes the incidence angle when the light amount of the reflected light (not illustrated) emitted from the light emission surface 23 is at a minimum in the case of scanning the incidence angle of the excitation light α to the metal film 30. In addition, the "enhancement angle" denotes the incidence angle when the light amount of the scattered light (hereinafter, referred to as "plasmon scattered light") β having the same wavelength as the excitation light α emitted above the sensing chip 10 is at a maximum in the case of scanning the incidence angle of the excitation light α to the metal film 30. For example, each of the angle between the incidence surface 21 and the film formation surface 22 and the angle between the film formation surface 22 and the light emission surface 23 is about 80°.

The prism 20 may have other elements as required. For example, the prism 20 may have a reagent holder for accommodating a reagent at a position which does not interfere with the optical path of the excitation light α.

Examples of materials for the prism 20 include resin and glass. Examples of the resin constituting the prism 20 include polymethylmethacrylate (PMMA), polycarbonate (PC), and a cycloolefin-based polymer. The prism 20 is preferably a resin having a refractive index of 1.4 to 1.6 and a small birefringence.

The metal film 30 is formed on one surface (film formation surface 22) of the prism 20. By providing the metal film 30, interaction (surface plasmon resonance; SPR) occurs between photons of the excitation light incident on the film formation surface 22 under the total reflection condition and free electrons in the metal film 30, so that it is possible to generate the localized field light on the surface of the metal film 30. The material of the metal film 30 is not particularly limited as long as the material of the metal film is a metal that generates surface plasmon resonance. Examples of the material of the metal film 30 include gold, silver, copper, aluminum, and alloys thereof. In the embodiment, the metal film 30 is a gold thin film. Although the thickness of the metal film 30 is not particularly limited, the thickness of the metal film is preferably in the range of 30 to 70 nm.

In addition, a capturer 60 for capturing the substance to be detected is immobilized on the surface of the metal film 30 not facing the prism 20. More specifically, the capturer 60 is immobilized on at least a portion of the inner wall surface of the first through-hole 41 of the first frame 40 and the surface of the metal film 30 exposed in the first through-hole 41 (refer to FIG. 4C described later). In addition, in FIG. 2B, in order to illustrate the second frame 50, the capturer 60 immobilized on the inner wall surface of the first through-hole 41 and the capturer 60 immobilized on the portion of the surface of the metal film 30 where the second frame 50 is arranged are omitted. By the capturer 60, it is possible to selectively detect the substance to be detected. At least a portion of the surface of the metal film 30 on which the capturer 60 is immobilized is set as a reaction field where a reaction such as binding (primary reaction) of the capturer 60 and the substance to be detected or fluorescence labeling (secondary reaction) of the substance to be detected is performed. In the embodiment, the surface of the metal film 30 exposed in the second through-hole 51 of the second frame 50 described later is set as a reaction field. The type of the capturer 60 is not particularly limited as long as the capturer can capture the substance to be detected. For example, the capturer 60 is an antibody or a fragment thereof capable of specifically binding to a substance to be detected.

The first frame 40 has the first through-hole 41 and is arranged on the prism 20 (the metal film 30) so that one opening of the first through-hole 41 is closed. When manufacturing the sensing chip 10 according to the embodiment, the first frame 40 defines a region on the metal film 30 where the capturer 60 is to be immobilized. The number, shape and size of the first through-holes 41 are not particularly limited and can be appropriately set according to the use of the sensing chip 10. In the embodiment, the number of the first through-holes 41 is one, and the shape of the first through-holes 41 is a cylindrical shape.

The first frame 40 preferably has a light blocking property. Therefore, by cutting noise light such as auto-fluorescence light emitted from the prism 20 or external light, it is possible to prevent the noise light from reaching the light receiving unit 130 of the SPFS apparatus 100.

The outer shape of the first frame 40 is not particularly limited. For example, the outer shape of the first frame 40 in a plan view is a circular shape, a quadrilateral shape, or the like. In the embodiment, the outer shape of the first frame 40 in a plan view is a quadrilateral shape.

The first frame 40 may have other elements as required. For example, as illustrated in FIGS. 2A and 2B, the first frame 40 may have a reagent holder 43 for accommodating reagents. The reagent holder 43 may be integral with the first frame 40 or may be a separate body. In the embodiment, the reagent holder 43 is integrated with the first frame 40.

Examples of the material of the first frame 40 include resin and glass. For example, the first frame 40 may be a resin film. Therefore, the manufacturing becomes easy, the manufacturing cost can be reduced, and the sensing chip 10 can be miniaturized.

The second frame 50 has a second through-hole 51 and is arranged on the prism 20 (the metal film 30) in the first through-hole 41 so that one opening of the second through-hole 51 is closed. The second frame 50 may be arranged so as to be in contact with the first frame 40 without a gap or may be arranged to be separated from the first frame. The second frame 50 defines the well 53 for accommodating the liquid. In addition, since the region (reaction field) where the substance to be detected is captured by the capturer 60 is defined by the second frame 50, the second frame 50 serves as a mark, and position adjustment of the irradiation position of the excitation light α in the SPFS apparatus 100 is facilitated.

The shape and size of the second through-hole 51 are not particularly limited and can be set appropriately according to the application. Examples of the shape of the second through-hole 51 include a cylindrical trapezoidal shape, a cylindrical shape, an elliptic cylindrical shape, a polygonal columnar shape, and combinations thereof. From the viewpoint of making it easier to remove the liquid in the well 53 and from the viewpoint of ease of processing the second frame 50, it is preferable that the shape of the second through-hole 51 is a cylindrical shape or an elliptic cylindrical shape. In the embodiment, the shape of the second through-hole 51 is a combination of a cylindrical shape and a cylindrical trapezoidal shape.

As illustrated in FIG. 2B, the depth h2 of the second through-hole 51 is preferably higher than the height h1 of the first through-hole 41. Therefore, it is possible to prevent the liquid from scattering out of the well 53 in a case where the liquid is fed into the well 53. The height of the second through-hole 51 can be appropriately set according to the height and amount of the fed liquid bouncing back from the metal film 30 and the inner wall surface of the second through-hole 51.

The outer shape of the second frame 50 is not particularly limited. For example, the outer shape of the second frame 50 in a plan view is a circular shape, a quadrilateral shape, or the like. In the embodiment, the outer shape of the second frame 50 in a plan view is a circular shape. In addition, it is preferable that the second frame 50 has a tapered portion where the cross-sectional area of the second through-hole 51 increases in the direction perpendicular to the height direction of the second through-hole 51 as the distance from the prism 20 increases. Therefore, it is possible to easily supply the liquid into the second through-hole 51 (the well 53). In the embodiment, the second frame 50 has a tapered portion 52.

In a case where the second frame 50 has the tapered portion 52, it is further preferable that the inner wall surface of the tapered portion 52 is inclined so that the light beam emitted from the center of the surface (reaction field) of the metal film 30 exposed in the second through-hole 51 and emitted at an emitting angle of 20° or less is not blocked. Therefore, it is possible to prevent the fluorescence light γ emitted from the fluorescent substance labeling the substance to be detected from being blocked, so that it is possible to detect the substance to be detected with high accuracy.

It is preferable that the inner wall surface of the second through-hole 51 is subjected to a blocking treatment. Therefore, it is possible to suppress non-specific binding of the substance to be detected to the inner wall surface of the second through-hole 51, so that it is possible to improve the detection efficiency of the substance to be detected.

In addition, the second frame 50 may have other elements as required. For example, the second frame 50 may have a reagent holder for accommodating the reagent.

The shape and color of the inner wall surface of the second frame 50 can be appropriately set as required. For example, in a case where a large amount of noise light is included in the detected light, the inner wall surface of the second frame 50 may be configured to be black from the viewpoint of absorbing excessive noise light. In addition, in a case where the noise light has directionality, the inner wall surface of the second frame 50 may be configured to have minute irregularities from the viewpoint of dispersing noise light to reduce noise. In addition, the inner wall surface of the second frame 50 may be configured to be white, or the inner wall surface of the second frame 50 may be configured to be a mirror surface from the viewpoint of reflecting the fluorescence light γ emitted from the fluorescent substance labeling the substance to be detected toward the light receiving unit 130.

Examples of the material of the second frame 50 include resin and glass. For example, the second frame 50 may be a resin film. Therefore, the manufacturing becomes easy, the manufacturing cost can be reduced, and the sensing chip 10 can be miniaturized.

The second frame 50 is bonded to the metal film 30 or the prism 20 by, for example, bonding with double-sided tape or adhesive, laser welding, ultrasonic welding, crimping using a clamp member, or the like. In addition, the second frame 50 may be bonded to the first frame 40.

As illustrated in FIG. 1, the excitation light α guided to the prism 20 is incident on the incidence surface 21 into the prism 20. The excitation light α incident into the prism 20 is incident on the interface (film formation surface 22) between the prism 20 and the metal film 30 so that a total reflection angle (the angle at which surface plasmon resonance occurs) is formed. The reflected light reflected at the interface is emitted to the outside of the prism 20 from the light emission surface 23 (not illustrated). At this time, the excitation light α is incident on the interface at the angle at which the surface plasmon resonance occurs, so that the plasmon scattered light β, the fluorescence light γ from the fluorescent substance, and the like are emitted above the sensing chip 10 from the reaction field.

(Method of Manufacturing Sensing Chip)

Figure 3:
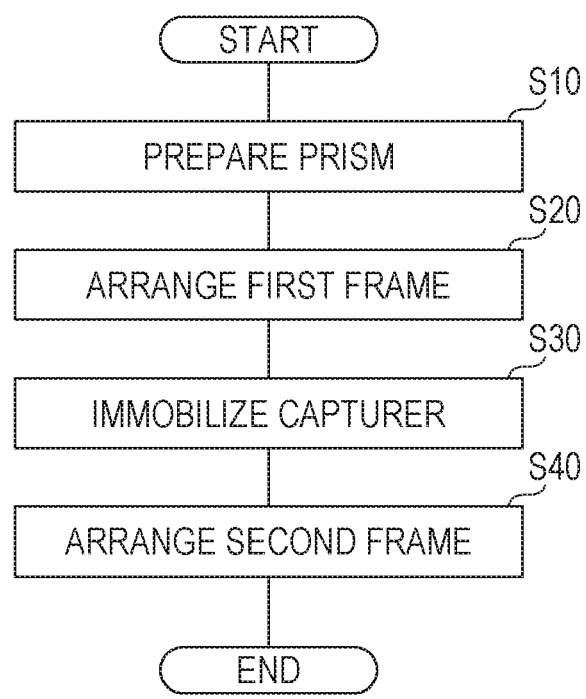
FIG. 3 is a flowchart illustrating an example of processes of manufacturing a sensing chip according to an embodiment of the present invention.

Next, an example of a method of manufacturing the sensing chip 10 according to the embodiment will be described. FIG. 3 is a flowchart illustrating an example of processes of manufacturing the sensing chip 10 according to the embodiment. FIGS. 4A to 4D are schematic diagrams illustrating an example of the processes of manufacturing the sensing chip 10 according to the embodiment.

For example, the sensing chip 10 according to the embodiment can be manufactured by performing a first step (step S10) of preparing the prism 20, a second step (step S20) of arranging the first frame 40 on the prism 20 (metal film 30)), a third step (step S30) of immobilizing the capturer 60 on the metal film 30 exposed in the first through-hole 41, and a fourth step (step S40) of arranging the second frame 50 in the first through-hole 41.

1) First Step

Figure 4A:
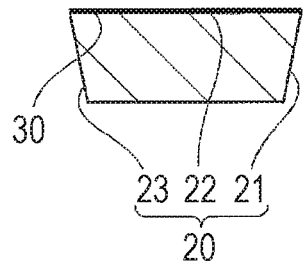
FIGS. 4A to 4D are schematic diagrams illustrating an example of processes of manufacturing a sensing chip according to an embodiment of the present invention.

In the first step, as illustrated in FIG. 4A, the prism 20 (support) having the incidence surface 21, the film formation surface 22, and the light emission surface 23 and having the metal film 30 formed on one surface (film formation surface 22) is prepared (step S10). First, the prism 20 is molded into a desired shape. A method of molding the prism 20 is not particularly limited, and for example, the prism 20 may be molded by a die molding method. Next, the metal film 30 is formed on the film formation surface 22 of the prism 20. Examples of a method of forming the metal film 30 include sputtering, vapor deposition, and plating. Alternatively, the prism 20 on which the metal film 30 has already been formed may be purchased.

2) Second Step

Figure 4B:
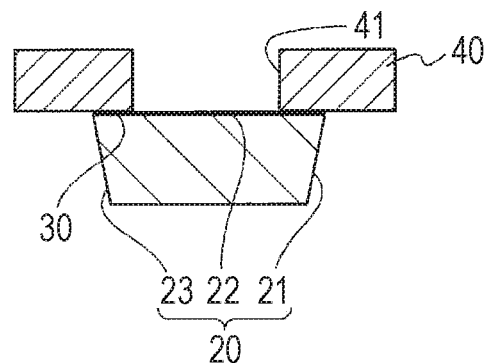

In the second step, as illustrated in FIG. 4B, the first frame 40 having the first through-hole 41 is arranged on the metal film 30 so that one opening of the first through-hole 41 is closed (step S20). A method of forming the first through-hole 41 in the first frame 40 is not particularly limited, and the first through-hole 41 may be formed by, for example, a die molding method, a cutting process, or the like.

3) Third Step

Figure 4C:
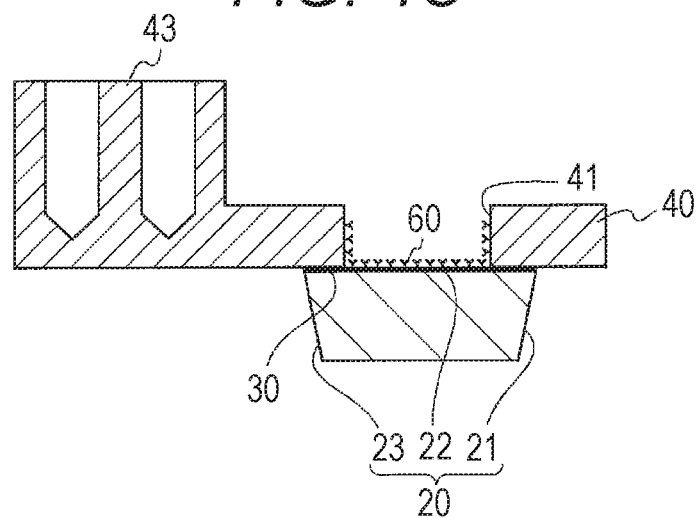

In the third step, as illustrated, in FIG. 4C, the capturer 60 is immobilized on the metal film 30 exposed in the first through-hole 41 (step S30). Specifically, a liquid containing the capturer 60 is fed into the first through-hole 41 of the first frame 40 arranged on the metal film 30. Therefore, the capturer 60 is immobilized on at least a portion of the inner wall surface of the first through-hole 41 of the first frame 40 which is in contact with the fed liquid and the surface of the metal film 30 exposed in the first through-hole 41.

In addition, a method of immobilizing the capturer 60 on the metal film 30 is not particularly limited. For example, a self-assembled monolayer (hereinafter, referred to as "SAM") or a polymer membrane to which the capturer 60 is bonded may be formed on the metal film 30. Examples of the SAM include membranes formed with substituted aliphatic thiols such as $HOOC-(CH_2)_{11}-SH$. Examples of materials constituting the polymer membrane include polyethylene glycol and MPC polymers. In addition, a polymer having a reactive group (or a functional group convertible to a reactive group) capable of being bonded to the capturer 60 may be immobilized on the metal film 30, and the capturer 60 may be bonded to the polymer.

4) Fourth Step

Figure 4D:
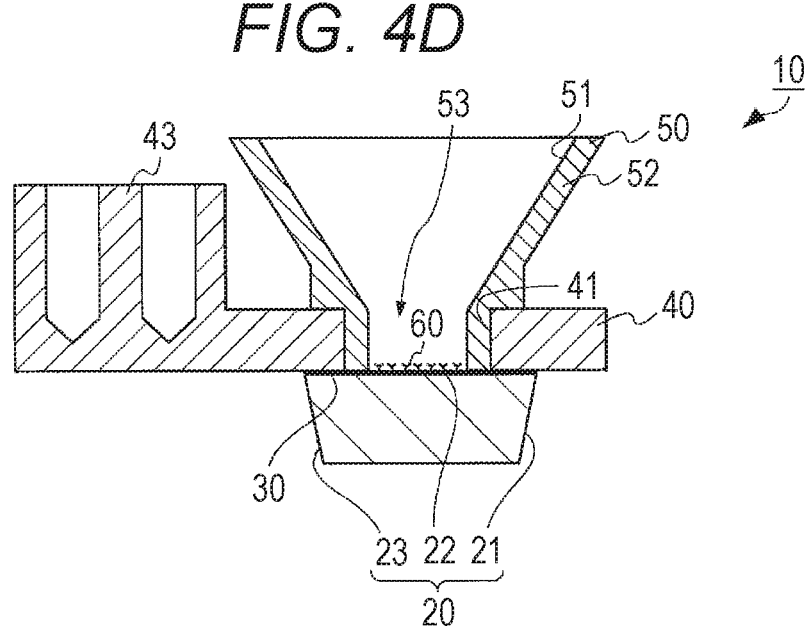

In the fourth step, after removing the liquid containing the capturer 60 from above the metal film 30, as illustrated in FIG. 4D, the second frame 50 having the second through-hole 51 is arranged on the metal film 30 in the first through-hole 41 so that one opening of the second through-hole 51 is closed (step S40). Typically, after removing the liquid containing the capturer 60, before arranging the second frame 50, the inside of the first through-hole 41 is cleaned with a buffer solution or the like. In addition, although not illustrated in FIG. 41D, even if the second frame 50 is arranged in the first through-hole 41, the capturer 60 is immobilized on a portion of the inner wall surface of the first through-hole 41 of the first frame 40 and the surface of the metal film 30. The second through-hole 51 can be formed by, for example, the same method as the first through-hole 41.

Through the above-mentioned steps, the sensing chip 10 used for detecting the substance to be detected contained in the specimen can be manufactured.

As an arbitrary step, a step of performing a blocking treatment on the second frame 50 may be further included. In the blocking treatment, for example, a liquid containing a blocking agent may be brought into contact with the inner wall surface of the second frame 50. The blocking treatment may be performed in advance before the second frame 50 is arranged on the metal film 30 or after the second frame 50 is arranged on the metal film 30. Examples of blocking agents include high molecular weight compounds such as casein, skim milk, albumin (including bovine serum albumin), gelatin, polyethylene glycol, and the like, low molecular weight compounds such as phospholipids, ethylenediamine and acetonitrile, and the like. These blocking agents may be used alone or in combination of two or more.

In addition, as an arbitrary step, a step of protecting the capturer 60 with a moisturizing agent may be included to prevent the capturer 60 from drying out.

In the sensing chip 10 according to the embodiment manufactured in this manner, the capturer 60 is also immobilized on a portion of the inner wall surface of the first through-hole 41 of the first frame 40. However, since the second frame 50 arranged in the inside of the first through-hole 41 defines the well 53, the liquid introduced into the well 53 will not be in contact with the inner wall surface of the first through-hole 41. In addition, the capturer 60 is not immobilized on the inner wall surface of the second through-hole 51 of the second frame 50. Therefore, in a case where a specimen is introduced into the well 53, the substance to be detected contained in the specimen is efficiently captured by the capturer 60 immobilized on the bottom surface of the well 53.

(Configuration of SPFS Apparatus)

Next, each component of the SPFS apparatus 100 will be described. As described above, the SPFS apparatus 100 is configured to include the chip holder 110, the light irradiation unit 120, the light receiving unit 130, and the control unit 140 (refer to FIG. 1).

The chip holder 110 holds the sensing chip 10 at a predetermined position. The sensing chip 10 is irradiated with the excitation light α from the light irradiation unit 120 in the state where the sensing chip is held by the chip holder 110.

The light irradiation unit 120 irradiates the incidence surface 21 of the prism 20 of the sensing chip 10 held by the chip holder 110 with the excitation light α (single mode laser light). More specifically, the light source unit 121 emits the excitation light α to a region corresponding to the well 53 on the back surface of the metal film 30 so that a total reflection angle is formed.

The light irradiation unit 120 is configured to include a light source unit 121 that emits the excitation light α, an angle adjustment unit 122 that adjusts the incidence angle of the excitation light α to the interface (film formation surface 22) between the prism 20 and the metal film 30, and a light source control unit 123 that controls various devices included in the light source unit 121.

The light source unit 121 emits the excitation light α. For example, the light source unit 121 has a light source of the excitation light α, a beam shaping optical system, an APC mechanism, and a temperature adjustment mechanism (all the components are not illustrated).

The type of the light source is not particularly limited. Examples of type of light source include laser diodes (LD), light emitting diodes, mercury lamps, and other laser light sources.

In a case where the excitation light α emitted from the light source is not a beam, the excitation light α emitted from the light source is converted into a beam by a lens, a mirror, a slit, or the like. In addition, in a case where the excitation light α emitted from the light source is not monochromatic light, the excitation light α emitted from the light source is converted into monochromatic light by a diffraction grating or the like. Furthermore, in a case where the excitation light α emitted from the light source is not linearly polarized light, the excitation light α emitted from the light source is converted into linearly polarized light by a polarizer or the like.

The beam shaping optical system is configured to include, for example, a collimator, a band pass filter, a linear polarizing filter, a half wave plate, a slit, a zoom means, and the like. The beam shaping optical system may include all or some of the components.

The collimator collimates the excitation light α emitted from the light source.

The band pass filter converts the excitation light α emitted from the light source intro narrow band light having only the center wavelength. This is because the excitation light α from the tight source has a slight wavelength distribution width.

The linear polarizing filter converts the excitation light α emitted from the light source into completely linearly polarized light. The half-wave plate adjusts the polarization direction of the excitation light α so that the P-wave component light is incident on the metal film 30. The slit and the zooming means adjust the beam diameter and contour shape of the excitation light α so that the shape of the irradiation spot on the back surface of the metal film 30 becomes a circle having a predetermined size.

The APC mechanism controls the light source so that the output of the light source is constant. More specifically, the APC mechanism detects the light amount of light branched from the excitation light α with a photodiode (not illustrated) or the like. Then, the APC mechanism controls the output of the light source to be constant by controlling the input energy with a recursion circuit.

The temperature adjustment mechanism is, for example, a heater or a Peltier element. The wavelength and energy of the light emitted from the light source may vary depending on the temperature. Therefore, by maintaining the temperature of the light source constant by the temperature adjustment mechanism, the wavelength and the energy of the light emitted from the light source are controlled to be constant.

The angle adjustment unit 122 adjusts the incidence angle of the excitation light α to the metal film 30 (the interface (film formation surface 22) between the prism 20 and the metal film 30). The angle adjustment unit 122 rotates the optical axis of the excitation light α and the chip holder 110 relative to each other in order to irradiate a predetermined position of the metal film 30 (film formation surface 22) with the excitation light α at a predetermined incidence angle. In the embodiment, the angle adjustment unit 122 rotates the light source unit 121 around an axis (an axis perpendicular to the paper surface of FIG. 1) perpendicular to the optical axis of the excitation light α the metal film 30.

The light source control unit 123 controls various devices included in the light source unit 121 to adjust the power of the excitation light α from the light source unit 121, the irradiation time, and the like. The light source control unit 123 is configured with, for example, a well-known computer, microcomputer, or the like including an arithmetic device, a control device, a storage device, an input device, and an output device.

The light receiving unit 130 is arranged so as to face a surface of the metal film 30 of the sensing chip 10 held by the chip holder 110, which does not face the prism 20. The light receiving unit 130 detects the light (plasmon scattered light β or fluorescence light γ) emitted from the metal film 30 in the second through-hole 51. The tight receiving unit 130 is configured to include a first lens 132, an optical fitter 133, a second lens 134, and a light receiving sensor 135 which are arranged in the light receiving optical system unit 131, a position switching mechanism 136, and a light sensor control unit 137.

The first lens 132 is, for example, a condenser lens and condenses the light emitted from the metal film 30. The second lens 134 is, for example, an imaging lens and focuses the light condensed by the first lens 132 on the light receiving surface of the light receiving sensor 135. The optical paths between the two lenses are substantially parallel.

The optical filter 133 is arranged between the first lens 132 and the second lens 134. The optical filter 133 transmits only the fluorescence light component of the incident light, and removes the excitation light component (plasmon scattered light β). By removing the excitation light component by the optical filter 133, it is possible to detect the fluorescence light γ with a high S/N ratio. Examples of types of the optical filter 133 include an excitation light reflection filter, a short wavelength cut filter, and a band pass filter.

The light receiving sensor 135 detects the plasmon scattered light β and the fluorescence light γ emitted from the sensing chip 10. The type of the light receiving sensor 135 is not particularly limited as tong as the above object can be achieved, but it is preferable that the variation of the detection value is small even if the received tight amount increases. The light receiving sensor 135 is, for example, a photodiode (PD).

The position switching mechanism 136 switches the position of the optical filter 133 onto the optical path or out of the optical path in the light receiving optical system unit 131. Specifically, when the optical blank value or the fluorescence value is to be measured, the optical filter 133 is arranged on the optical path in the light receiving optical system unit 131, and when the light receiving sensor 135 is to detect the plasmon scattered light 3, the optical filter 133 is arranged out of the optical path.

The light sensor control unit 137 controls detecting the output value of the light receiving sensor 135 and managing the sensitivity of the light receiving sensor 135 based on the detected output value and controls the sensitivity of the light receiving sensor 135 to obtain an appropriate output value. The light sensor control unit 137 is configured with, for example, a well-known computer, microcomputer, or the like including an arithmetic device, a control device, a storage device, an input device, and an output device.

The control unit 140 controls the angle adjustment unit 122, the light source control unit 123, the position switching mechanism 136, and the light sensor control unit 137. The control unit 140 also functions as a processing unit for calculating a signal value indicating the presence or amount of the substance to be detected based on a detection result of the light receiving sensor 135. The control unit 140 is configured with, for example, a well-known computer, microcomputer, or the like including an arithmetic device, a control device, a storage device, an input device, and an output device.

[Operation of SPFS Apparatus]

Figure 5:
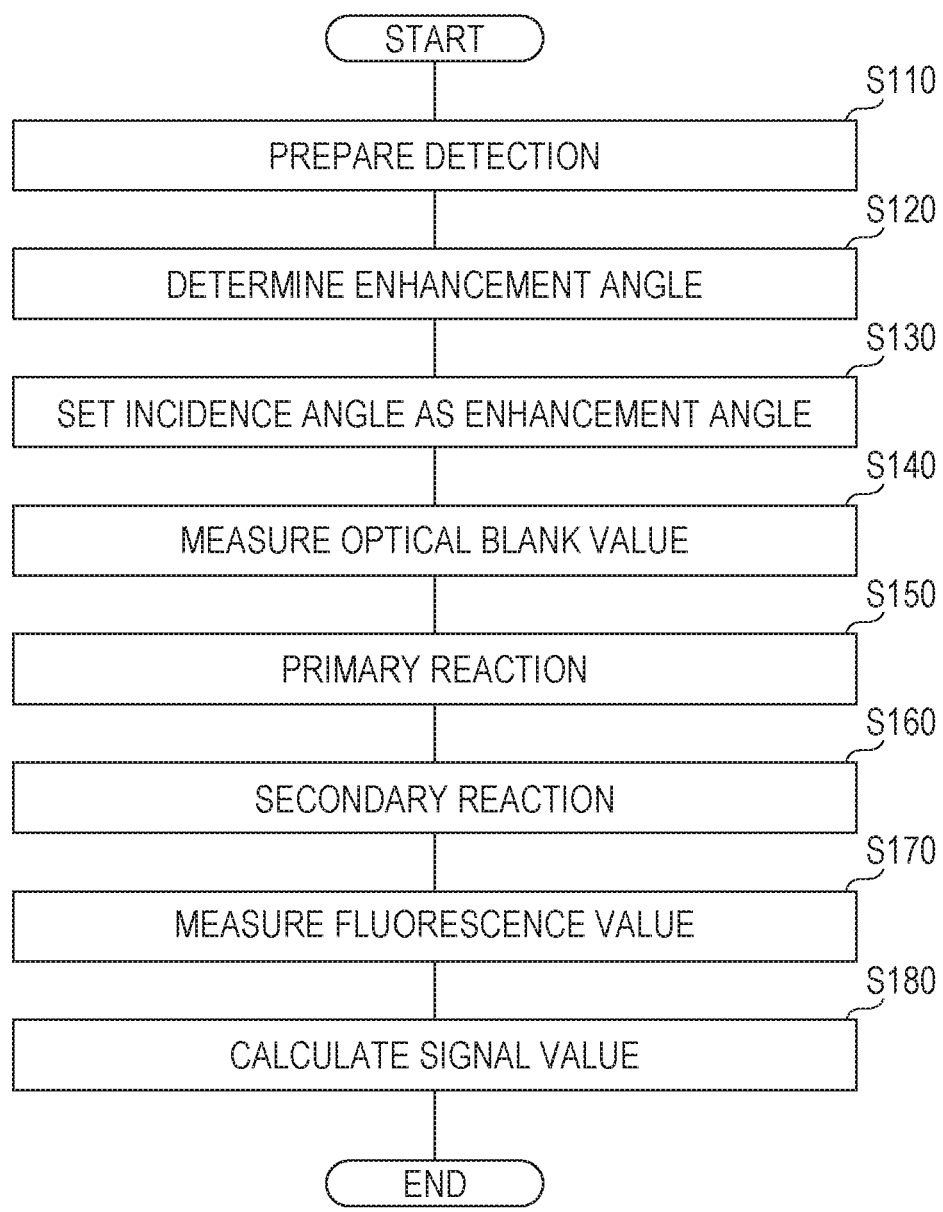
FIG. 5 is a flowchart illustrating an example of an operation procedure of a surface plasmon enhanced fluorescence detection apparatus.

Next, operations of the SPFS apparatus 100 using the sensing chip 10 will be described. FIG. 5 is a flowchart illustrating an example of the operation procedure of the SPFS apparatus.

First, detection is prepared (step S110). Specifically, the sensing chip 10 is installed in the chip holder 110 of the SPFS apparatus 100. In a ease where a moisturizing agent is present in the well 53 of the sensing chip 10, the interior of the well 53 is cleaned so as to remove the moisturizing agent so that the capturer 60 can appropriately capture the substance to be detected.

Next, the enhancement angle is determined (step S120). Specifically, while irradiating the predetermined position of the metal film 30 (film formation surface 22) with the excitation light α, the incidence angle of the excitation light α on the metal film 30 (film formation surface 22) is scanned to determine an optimum incidence angle. The control unit 140 controls the light source control unit 123 and the angle adjustment unit 122 to scan the incidence angle of the excitation light α to the metal film 30 (film formation surface 22) while irradiating the predetermined position of the metal film 30 (film formation surface 22) with the excitation light α from the light source unit 121. At this time, the control unit 140 controls the position switching mechanism 136 to move the optical filter 133 to the outside of the optical path of the light receiving optical system unit 131. At the same time, the control unit 140 controls the light sensor control unit 137 to detect the plasmon scattered light β with the light receiving sensor 135. The control unit 140 obtains data including the relationship between the incidence angle of the excitation light α and the intensity of the plasmon scattered light β. Then, the control unit 140 analyzes the data and determines the incidence angle (enhancement angle) at which the intensity of the plasmon scattered light β becomes maximum. In addition, although the enhancement angle is determined by the material and shape of the prism 20, the thickness of the metal film 30, the refractive index of the liquid in the well 53, and the like, the enhancement angle varies slightly depending on various factors such as the type and amount of the capturer 60 and the shape error of the prism 20. Therefore, it is preferable to determine the enhancement angle each time the detection is performed. The enhancement angle is determined on the order of about 0.1°.

Next, the incidence angle of the excitation light α to the metal film 30 (film formation surface 22) is set to be the enhancement angle determined in step S120 (step S130). Specifically, the control unit 140 controls the angle adjustment unit 122 to set the incidence angle of the excitation light α to the metal film 30 (film formation surface 22) to be the enhancement angle. In the subsequent steps, the incidence angle of the excitation light α to the metal film 30 (film formation surface 22) is the enhancement angle.

Next, in the state where no fluorescent substance is present on the metal film 30, detection of light including light having the same wavelength as the fluorescence light γ is performed, and the optical blank value is measured (step S140). Herein, the "optical blank value" denotes the light amount of background light emitted above the sensing chip 10. This background tight is mainly caused by auto-fluorescence light emitted from the sensing chip 10 (prism 20) and external light in the irradiation with the excitation light α.

Specifically, the control unit 140 controls the position switching mechanism 136 to move the optical filter 133 onto the optical path of the light receiving optical system unit 131. Next, the control unit 140 controls the light source control unit 123 to irradiate the metal film 30 with the excitation light α through the prism 20 from the light source unit 121 so that the surface plasmon resonance occurs in the metal film 30 in the state where there is no fluorescent substance on the metal film 30. At the same time, the control unit 140 controls the light sensor control unit 137 to detect the light emitted from the sensing chip 10 by the light receiving sensor 135 and obtains the optical blank value. The measured optical blank value is transmitted to and stored in the control unit (processing unit) 140.

Subsequently, the substance to be detected in the specimen and the capturer 60 are allowed to react with each other (primary reaction; step S150). Specifically, the specimen is injected into the well 53, and the specimen and the capturer 60 are brought into contact with each other. In a case where a substance to be detected is present in the specimen, at least a portion of the substance to be detected is captured by the capturer 60. At this tittle, the substance to be detected is appropriately captured by the capturer 60 immobilized on the bottom surface of the well 53. The capturer 60 is also immobilized on a portion of the inner wall surface of the first through-hole 41 of the first frame 40, but contact between the capturer 60 immobilized at a position other than the bottom surface of the well 53 and the specimen is hindered by the second frame 50. In addition, on the inner wall surface of the second through-hole 51 of the second frame 50, the capturer 60 is not immobilized. Therefore, the substance to be detected is efficiently captured by the capturer 60 immobilized on the bottom surface of the well 53. After that, the interior of the well 53 is cleaned with a buffer solution or the like to remove substances not captured by the capturer 60. The type of the specimen is not particularly limited. Examples of the specimens include body fluids such as blood and serum, plasma, urine, nostrils, saliva, semen and diluents thereof.

Subsequently, the substance to be detected captured by the capturer 60 is labeled with a fluorescent substance (secondary reaction; step S160). Specifically, a fluorescent labeling solution is fed into the well 53. The fluorescent labeling solution is, for example, a buffer solution containing an antibody (secondary antibody) labeled with the fluorescent substance. When the fluorescent labeling solution is fed into the well 53, the fluorescent labeling solution comes into contact with the substance to be detected captured by the capturer 60, so that the substance to be detected is labeled with the fluorescent substance. Thereafter, the inside of the well 53 is cleaned with a buffer solution or the like to remove free fluorescent substances and the like.

Next, in the state where the substance to be detected labeled with a fluorescent substance is present in the well 53, by irradiating the metal film 30 (film formation surface 22) with the excitation light α and detecting the fluorescence light γ emitted from the fluorescent substance that labels the substance to be detected in the reaction field, the fluorescence value is measured (step S170). Specifically, the control unit 140 controls the light source control unit 123 to allow the excitation light α to be emitted from the light source unit 121 to the metal film 30 through the prism 20 so that the surface plasmon resonance occurs in the metal film 30 in the state where the substance to be detected labeled with the fluorescent substance is present on the metal film 30. At the same time, the control unit 140 controls the light sensor control unit 137 to detect the fluorescence light γ emitted from the fluorescent substance labeling the substance to be detected with the light receiving sensor 135. The measured fluorescence value is transmuted to the control unit (processing unit) 140 and stored.

Finally, a signal value indicating the presence or amount of the substance to be detected is calculated (step S180). Specifically, the control unit 140 calculates a signal value correlating to the amount of the substance to be detected by subtracting the optical blank value obtained in step S140 from the fluorescence value obtained in step S170. The signal value can be reduced into the amount or concentration of the substance to be detected by a calibration curve prepared in advance.

By performing the above-described operation procedure, it is possible to detect the substance to be detected with high accuracy by using the sensing chip 10 according to the embodiment.

In addition, the order of steps S120 to S180 is not limited to the above order. For example, after performing the primary, reaction (step S150), the determining of the enhancement angle (step S120), the setting of the incidence angle to the enhancement angle (step S130) and the measuring of the optical blank value (step S140) may be performed.

(Effect)

As described above, by using the sensing chip 10 according to the embodiment, it is possible to suppress the adhesion of the substance to be detected to the inner wall surface of the well 53 and to reduce the number of substances to be detected that are not detected. Therefore, it is possible to detect the substance to be detected in the specimen with high accuracy.

Figure 6A:
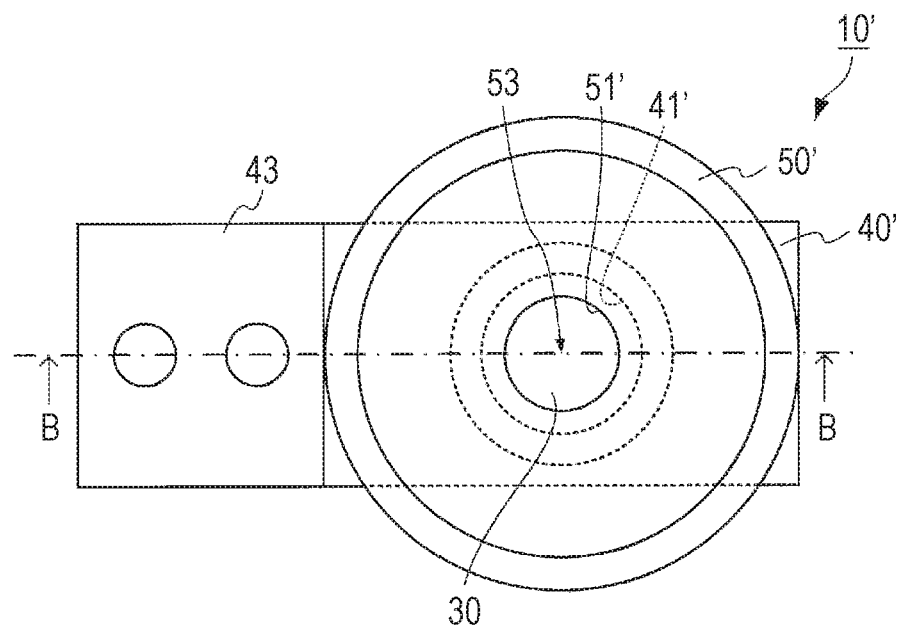
FIGS. 6A and 6B are diagrams illustrating a configuration of a sensing chip according to Modified Example 1.
Figure 6B:
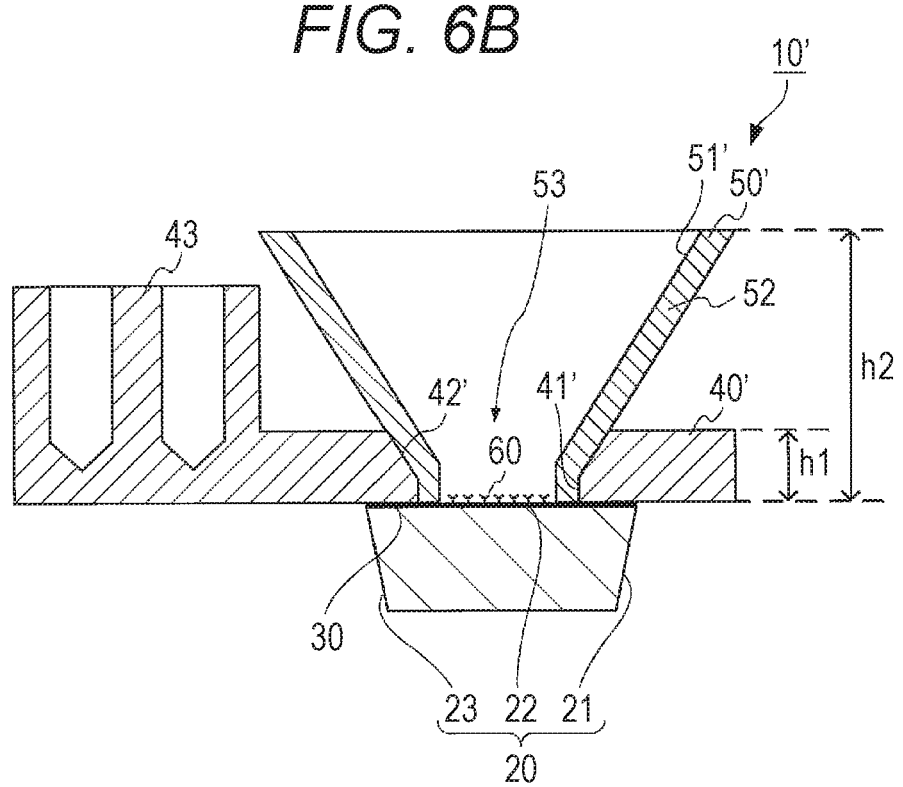

In addition, in the above-described embodiment, the sensing chip 10 having the first frame 40 of which the shape of the first through-hole 41 is a cylindrical shape has been described. However, the shape of the first frame 40 in the sensing chip 10 according to the embodiment is not limited thereto. FIGS. 6A and 6B are diagrams illustrating a configuration of a sensing chip 10' according to Modified Example 1. FIG. 6A is a plan diagram of the sensing chip 10', and FIG. 6B is a cross-sectional diagram taken along the line B-B in FIG. 6A. As illustrated in FIGS. 6A and 6B, the first frame 40' may have a tapered portion 42' so that, as the first frame 40' is away from the prism 20, the cross-sectional area of the first through-hole 41' in the direction perpendicular to the height direction of the first through-hole 41' increases. Therefore, it is possible to easily feed a liquid (for example, a liquid containing the capturer 60, a cleaning liquid, or the like) in the first through-hole 41'. In addition, in the sensing chip 10' according to Modified Example 1, a second frame 50' may be arranged so as to be in contact with the first frame 40' without a gap or may be arranged to be separated from the first frame. In the sensing chip 10' according to Modified Example 1, the shape of the second frame 50' (the second through-hole 51') is formed so as to be in contact with the first frame 40' without a gap.

Figure 7A:
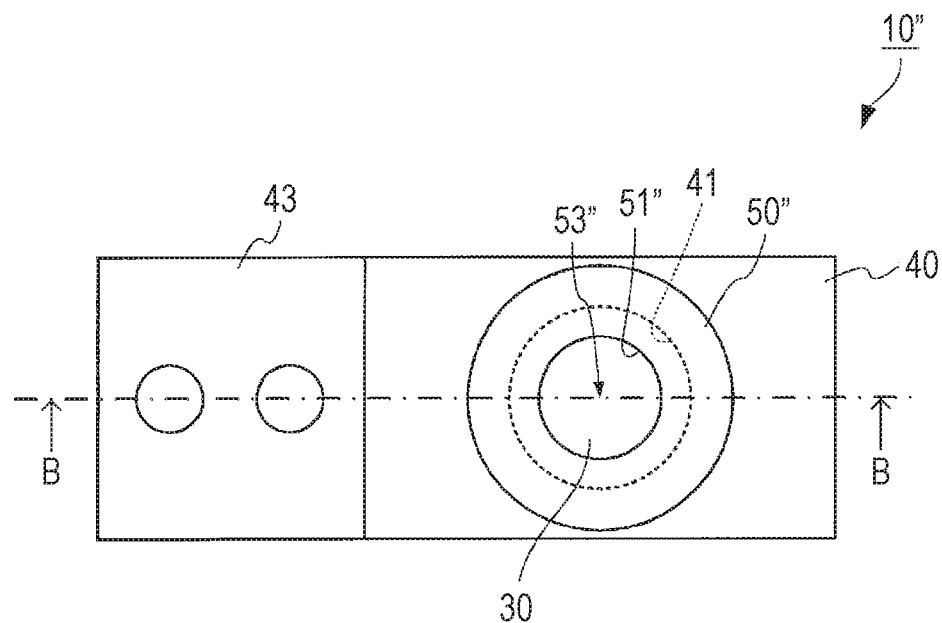
FIGS. 7A and 7B are diagrams illustrating a configuration of a sensing chip according to Modified Example 2.
Figure 7B:
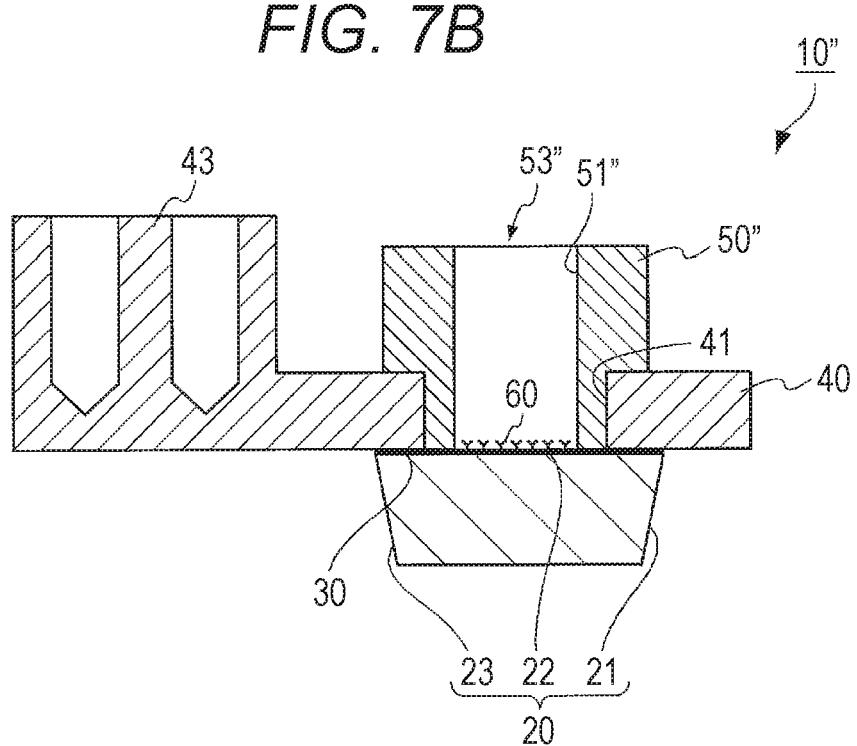

In addition, in the above-described embodiment, the sensing chip 10 having the second frame 50 including the tapered portion has been described. However, the shape of the second frame of the sensing chip 10 according to the present invention is not limited thereto. FIGS. 7A and 7B are diagrams illustrating a configuration of a sensing chip 10" according to Modified Example 2. FIG. 7A is a plan diagram of the sensing chip 10", and FIG. 7B is a cross-sectional diagram taken along the line B-B in FIG. 7A. As illustrated in FIGS. 7A and 7B, a second through-hole 51" of a second frame 50" may have a cylindrical shape. In the sensing chip 10" according to Modified Example 2, the shape of a well 53" is a cylindrical shape. Also in this case, the same effects as the above-described embodiment can be obtained by manufacturing the sensing chip 10" similarly to the above-described embodiment.

In addition, in the above-described embodiment, a case where the sensing chips 10, 10', and 10" are used for detecting the substance to be detected by using the SPFS has been described. However, the sensing chip according to the present invention is not limited thereto, and the sensing chip can be used for other immunoassays. In this case, a support such as a glass substrate may be used instead of the prism 20 having the metal film 30 formed on one surface.

This application claims priority based on Japanese Patent Application No. 2015-087588 filed on Apr. 22, 2015. The entire contents described in the application specification and drawings are incorporated herein by reference.

INDUSTRIAL APPLICABILITY

According to a sensing chip of the present invention, since a substance to be detected can be detected with high sensitivity and high accuracy, the sensing chip is useful for, for example, clinical examinations.

REFERENCE SIGNS LIST

10, 10', 10" sensing chip
20 prism 21 incidence surface
22 film formation surface
23 light emission surface
30 metal film
40, 40' first frame
41, 41' first through-hole
50, 50', 50" second frame
51, 51', 51" second through-hole
42', 52 tapered portion
43 reagent holder
53, 53" well
60 capturer
100 surface plasmon resonance fluorescence analysis apparatus (SPFS apparatus)
110 chip holder
120 light irradiation unit
121 light source unit
122 angle adjustment unit
123 light source control unit
130 light receiving unit
131 light receiving optical system unit
132 first lens
133 optical filter
134 second lens
135 light receiving sensor
136 position switching mechanism
137 light sensor control unit
140 control unit (processing unit)
α excitation light
β plasmon scattered light
γ fluorescence light
h1 height of first through-hole
h2 height of second through-hole

The invention claimed is:

1. A sensing chip used for detecting a substance to be detected in a specimen, the chip comprising:
a support;
a first frame having a first through-hole formed through the first frame, the first frame being arranged on the support so that one opening of the first through-hole is closed; and
a second frame having a second through-hole formed through the second frame, the second frame being arranged on the support in the first through-hole so that one opening of the second through-hole is closed,
wherein a capturer for capturing the substance to be detected in the specimen is immobilized on at least a portion of an inner wall surface of the first through-hole of the first frame and on a surface of the support exposed in the first through-hole.

2. The sensing chip according to claim 1, wherein the first frame has a light blocking property.

3. The sensing chip according to claim 1, wherein the first frame comprises a tapered portion where a cross-sectional area of the first through-hole increases in a direction perpendicular to a height direction of the first through-hole in accordance with an increase in distance away from the support.

4. The sensing chip according to claim 1, wherein the second frame comprises a tapered portion where a cross-sectional area of the second through-hole increases in a direction perpendicular to a height direction of the second through-hole in accordance with an increase in distance away from the support.

5. The sensing chip according to claim 1, wherein a height of the second through-hole is larger than a height of the first through-hole.

6. The sensing chip according to claim 4, wherein an inner wall surface of the tapered portion of the second frame is inclined so that light emitted from a center of a surface of the support exposed in the second through-hole and emitted at an emitting angle of 20° or less is not blocked.

7. The sensing chip according to claim 1, wherein an inner wall surface of the second through-hole is subjected to a blocking treatment.

8. The sensing chip according to claim 1, wherein at least one of the support, the first frame, and the second frame has a reagent holder for accommodating a reagent.

9. The sensing chip according to claim 1, wherein at least one of the first frame and the second frame is made of a resin film.

10. The sensing chip according to claim 1, wherein:
the support comprises a prism made of a dielectric material and having a metal film formed on one surface thereof,
the first frame and the second frame are arranged on the one surface, and
the capturer is immobilized on at least a portion of an inner wall surface of the first through-hole of the first frame and on a surface of the metal film exposed in the first through-hole.

11. The sensing chip according to claim 1, wherein a portion of an outer circumferential surface of the second frame opposes an inner circumferential surface of the first through-hole.

* * * * *